(12) United States Patent
Tam et al.

(10) Patent No.: US 10,591,423 B1
(45) Date of Patent: Mar. 17, 2020

(54) INLINE FABRIC CONDUCTIVITY MEASUREMENT

(71) Applicants: Kent K. Tam, Rowland Heights, CA (US); Leon Burks, Jr., Los Angeles, CA (US); Mark D. Brown, San Pedro, CA (US)

(72) Inventors: Kent K. Tam, Rowland Heights, CA (US); Leon Burks, Jr., Los Angeles, CA (US); Mark D. Brown, San Pedro, CA (US)

(73) Assignee: NORTHROP GRUMMAN SYSTEMS CORPORATION, Falls Church, VA (US)

( * ) Notice: Subject to any disclaimer, the term of this patent is extended or adjusted under 35 U.S.C. 154(b) by 317 days.

(21) Appl. No.: 15/466,558

(22) Filed: Mar. 22, 2017

(51) Int. Cl.
*G01N 22/02* (2006.01)
*G01N 33/36* (2006.01)

(52) U.S. Cl.
CPC .......... *G01N 22/02* (2013.01); *G01N 33/367* (2013.01)

(58) Field of Classification Search
CPC ....... G01N 22/00; G01N 22/02; G01N 33/367
USPC ........................................................ 324/637
See application file for complete search history.

(56) References Cited

U.S. PATENT DOCUMENTS

| | | | |
|---|---|---|---|
| 4,334,030 A | 8/1982 | Anderson et al. | |
| 4,368,421 A * | 1/1983 | Glander | G01N 22/04 324/608 |
| 4,514,680 A | 4/1985 | Heikkila et al. | |
| 4,581,575 A | 4/1986 | Osaki et al. | |
| 4,841,223 A | 6/1989 | Baum et al. | |
| 4,885,527 A | 12/1989 | Lacombe et al. | |
| 5,128,621 A | 7/1992 | Berthaud et al. | |
| 5,497,100 A * | 3/1996 | Reiser | G01N 22/04 324/642 |
| 6,359,446 B1 | 3/2002 | Little, Jr. | |
| 6,422,741 B2 | 7/2002 | Murphy et al. | |
| 7,187,183 B2 | 3/2007 | Jonsson et al. | |
| 7,791,355 B1 | 9/2010 | Esher et al. | |
| 7,838,833 B1 | 11/2010 | Jez et al. | |

* cited by examiner

*Primary Examiner* — Reena Aurora
(74) *Attorney, Agent, or Firm* — Tarolli, Sundheim, Covell & Tummino LLP

(57) ABSTRACT

A non-destructive, inline, multi-channel fabric conductivity measurement system uses an array of opposing paired transmit/receive microwave horns on opposite sides of a fabric material moving in a production line, each horn pair corresponding to a channel in the system. A processor-based controller can control channel hopping, frequency hopping, and measurement orientation to acquire measurements of material conductivity and anisotropy, which measurements can be analyzed for defects that can be flagged in real time during production. Measurements and/or analyses can be stored to make roll-to-roll, batch-to-batch, day-to-day, or production-phase-to-production-phase comparisons useful in identifying the sources of production problems and/or the causes of corrections.

20 Claims, 4 Drawing Sheets

INLINE FABRIC CONDUCTIVITY MEASUREMENT

GOVERNMENT INTEREST

This invention was made with government support under contract N00019-02-C-3002 awarded by the United States Department of the Navy, Naval Air Systems Command, Patuxent River, Md. The government has certain rights in the invention.

TECHNICAL FIELD

The present invention relates to systems and methods for conductive materials fabrication testing, and more particularly to systems and methods for inline fabric conductivity measurement.

BACKGROUND

Systems and methods for quality assurance (QA) can test fabricated components or materials as they are manufactured to ensure that the fabrication process is producing components or materials having functional properties that fall within acceptable tolerances. The more tightly a QA system is integrated into the fabrication process, the better adapted it is to detect undesirable production line results and thus the more fit it is to rapidly make adjustments to the fabrication process and/or to detect flawed production line output for marking or segregation without delay or additional testing.

Electrical conductivity anisotropy is the property of a material to have directional dependence of its electrical conductivity. A material that is highly anisotropic may be electrically conductive in one direction but largely non-conductive in another direction.

SUMMARY

In one example, there is provided a system for non-destructive, inline, multi-channel fabric conductivity measurement. The system can include a processor-based controller communicatively coupled to various other elements of the system. One element may be a microwave signal source to produce signals at frequencies specified by the controller. Another element may be a transmit radio frequency (RF) switch to select one of a plurality of transmit microwave horns arranged in an array and route signals from the microwave signal source to a selected transmit microwave horn.

The system can also include an encoder to inform the controller of the speed of a production line. The production line can feed a fabric material between a plurality of pairs of opposing microwave horns comprising, on one side of the material, the transmit microwave horns and, on an opposing side of the material, a plurality of receive microwave horns arranged to each oppose a corresponding one of the transmit microwave horns. The controller can receive and record transmission measurements from at least one power sensor. The measurements can correspond to signals received from one of the plurality of receive microwave horns during periods of transmission from the transmit microwave horns.

The controller can control the microwave signal source and the transmit RF switch based on the production line speed. The controller can cycle through the plurality of horn pairs in rapid sequence, causing the transmit horn of each pair to, for example, emit a burst of microwave radiation at a selected frequency, or emit a chirp of microwave radiation over a specified frequency range. The cycle can occur sufficiently fast such that measurements are made of the location of the material between the horns before it can move an appreciable distance along the production line, providing complete measurement coverage of the material. The different horn pairs can also be of different polarity orientations, such that the measurement coverage is complete not only in terms of spatial location and frequency but also in terms of orientation of conductivity.

In another example, there is provided a method for non-destructive, inline, multi-channel fabric conductivity measurement. A processor-based controller can select a first microwave frequency and a first one of a plurality of transmit microwave horns. Microwave energy can be transmitted from the first transmit microwave horn at the first microwave frequency, through a conductive fabric material moving on a production line. The transmitted microwave energy cam be received by a first receive microwave horn placed to be paired with the first transmit microwave horn. The receive horn can be opposed to the transmit horn on the opposite side of the material from the transmit horn to form a first horn pair. The received microwave energy can be transduced into an electrical signal, and the electrical signal can be stored to a computer-readable memory as a first representation of the transduced received microwave energy. The repeating the selecting, transmitting, receiving, transducing, and storing can be repeated for additional horn pairs, and at additional frequencies, to yield additional stored representations. The representations can be analyzed to determine defects in the material, which can then be marked or labeled on the material at their locations.

In yet another example, there is provided a method of identifying a source of a defect in a manufacture of conductive fabric. During a first phase of manufacture of a sheet of conductive fabric, a first set of measurement data characterizing the conductivity and anisotropy of a plurality of locations on the sheet can be collected and stored. The sheet can be, for example, greater than one hundred feet in length. The measurement data can be based on detected microwave transmittance between a plurality of microwave transmit/receive horn pairs, each horn pair comprising a transmit horn and a receive horn positioned to oppose each other on opposite sides of the sheet. Then, during a second phase of manufacture, a second set of measurement data characterizing the conductivity and anisotropy of the plurality of locations on the sheet can be similarly collected and stored. Defects in the sheet can be determined based on the measurement data sets. The data sets can be compared to identify whether the defects were present in the first phase, the second phase, or both, and thus to narrow the source of the defects.

DETAILED DESCRIPTION

A spool of conductive fabric may range from fifty to hundreds of yards. Inspection of a spool after production is only practical at one end of the roll. The inline fabric conductivity measurement systems and methods described herein can achieve 100% inspection coverage of the production material. A non-contact sensor array can be employed, eliminating contamination of the material or interference with the production run.

Conductive fiber-mat materials are typically produced in 52" wide by hundreds of feet in length then prepregged and used in composite fabrication. Conductivity of these materials is derived from contacts of short conductive fibers such as metal coated graphite. Density, distribution, and orientation of these conductive fibers are deciding factors in the homogeneity of the material's electrical properties, including conductivity and anisotropy thereof. In some instances, the target material may be so conductive that an inspection system capable of a dynamic range of at least −65 dB or −70 dB may be required to inspect the material.

The systems and methods for inline fabric conductivity measurement described herein enable quality inspection while a conductive fiber-mat material is in the manufacturing process. Such systems and methods can provide real time feedback to operators to maintain the electrical and isotropy requirements during the manufacturing process. Effectively 100% surface inspection is achievable with the described systems and methods. Inline fabric conductivity measurement overcomes challenges in quality inspection of the finished product which may packaged, for example, in rolls of several hundred feet of material. Material not meeting production requirements can be flagged (e.g., not for use), or can be removed, creating subrolls of varying lengths. Furthermore, the systems and methods provided herein can be capable of dynamic ranges suitable for performing measurements on material that is extremely highly conductive.

Figure 1:
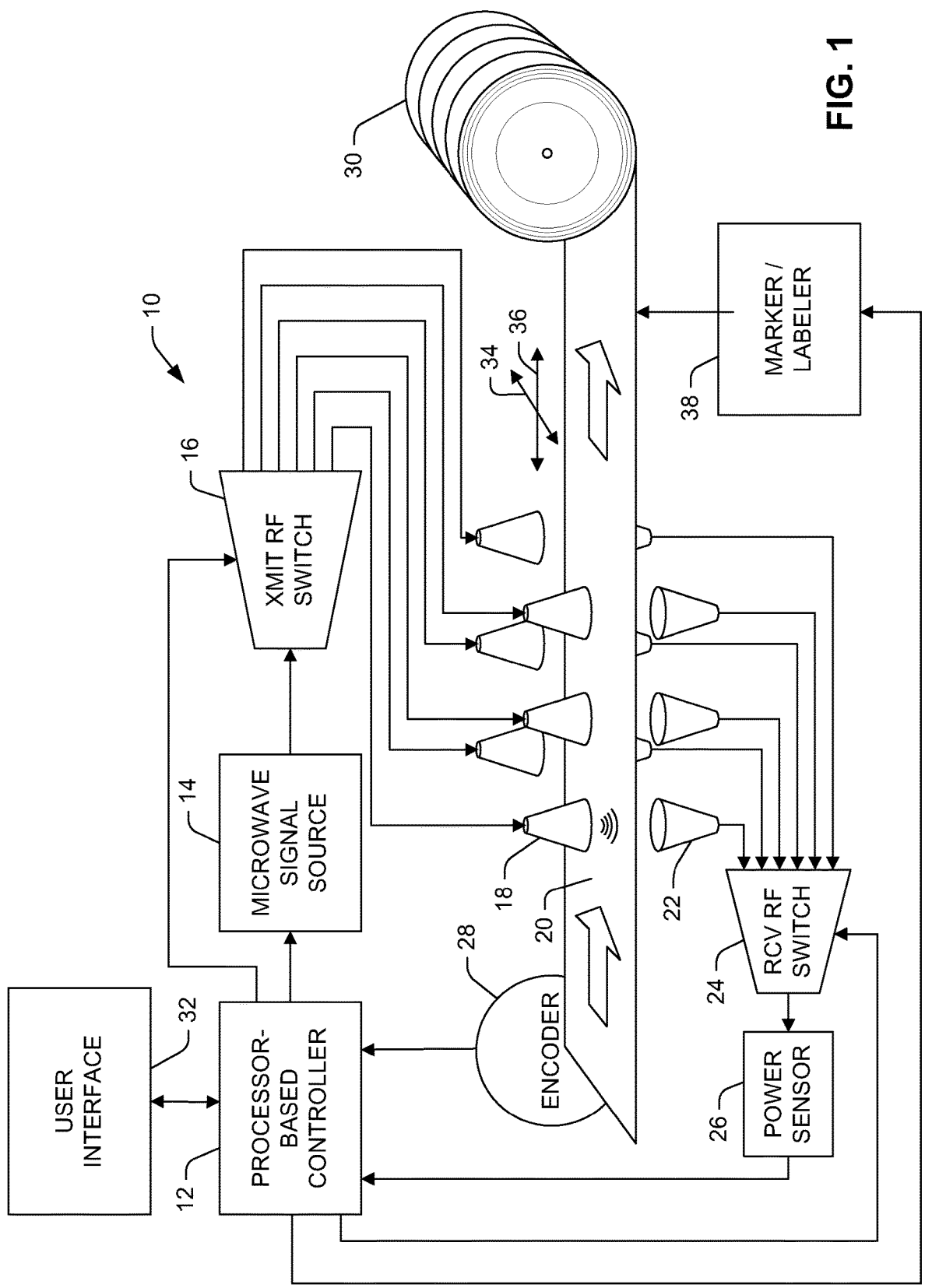
FIG. 1 illustrates an example of a system for inline fabric conductivity measurement.

In FIG. 1, an inline fabric conductivity measurement system 10 can include a processor-based controller 12, a microwave signal source 14, at least one power sensor 26, a and one or more radio-frequency (RF) switches 16, 24 to control selection of individual transmit/receive pairs chosen from among an array of transmission microwave horns 18 and reception microwave horns 18 arranged, respectively, above and below a manufactured material 20 traveling on a production line. The horns 18, 22 can be arranged to form an array of through transmission sensors. Each individual horn can be, for example, a 15 dB standard gain horn. The material 20 can be, for example, a conductive fabric, such as a fiber-mat or a composite prepreg, and can be collected in a roll or spool 30.

The transmit RF switch 16 can route signals of specified frequencies from the microwave signal source 14 to one of the horns 18 above the material 20 and can direct signals transmitted through the material 20, received by a horn below 22, to the power sensor 26. A receive switch 24 can mirror the function of transmit switch 16 so that power sensor 26 only receives signals from the particular receive horn 22 paired with the activated transmit horn 18 at any particular time.

Horns 18, 22 can be spaced evenly across the width of the material 20 such that a plurality of sensed microwave transmission signals can be detected. Each transmit-receive pair of horns can form a single channel of a multi-channel system 10. The selection of the type of horn and the placement of each horn may depend on the material being measured and the requirements of the testing. Generally, the larger the microwave horn, the greater the gain that can be provided by the horn. However, a tradeoff exists between horn size and number of horns used (i.e., horn placement density). The larger the size of horns selected, the fewer can be placed near each other in a pattern across the width of the material being tested. Horn size is described as a combination of 2-dimensional horn aperture size (horn width and horn height) and horn length. 15 dB standard gain horns can provide a suitable compromise between the number of horns and the gain that each horn can provide.

The horns can be placed in such close proximity to the material that stray radiation is effectively kept from getting into any individual channel. For example, the transmit horns 18 can be placed within 2.5 inches of one side of the material, without touching the material, and the receive horns can be placed within 2.5 inches of the opposite side of the material, without touching the material. In such examples, the total distance between a transmit horn and its counterpart receive horn will be about five inches. The free space opposing horns 18, 22 allow conductive material 20 to be measured with a dynamic range from, for example, −30 dB down to, for example, −70 dB in part because of such tight spacing, providing high quality measurements even in a production environment.

In some examples, the measurement system 10 can provide for adjustment of the height of the horns (i.e., their respective distances from the fabric). In some examples, the measurement system can provide for adjustment of the incident angles of the horns. In either instance, such adjustments can be, for example, lever-controlled, or servomotor controlled.

A sufficient number of horns 18, 22 can be placed at sufficient array density to collect data at an adequate spatial density of the moving material 20. For example, a pair of horns 18, 22 can be placed for every foot of material width. In such an example, for a four-foot wide roll of material, eight horn pairs can be placed along the width dimension 34.

Figure 2:
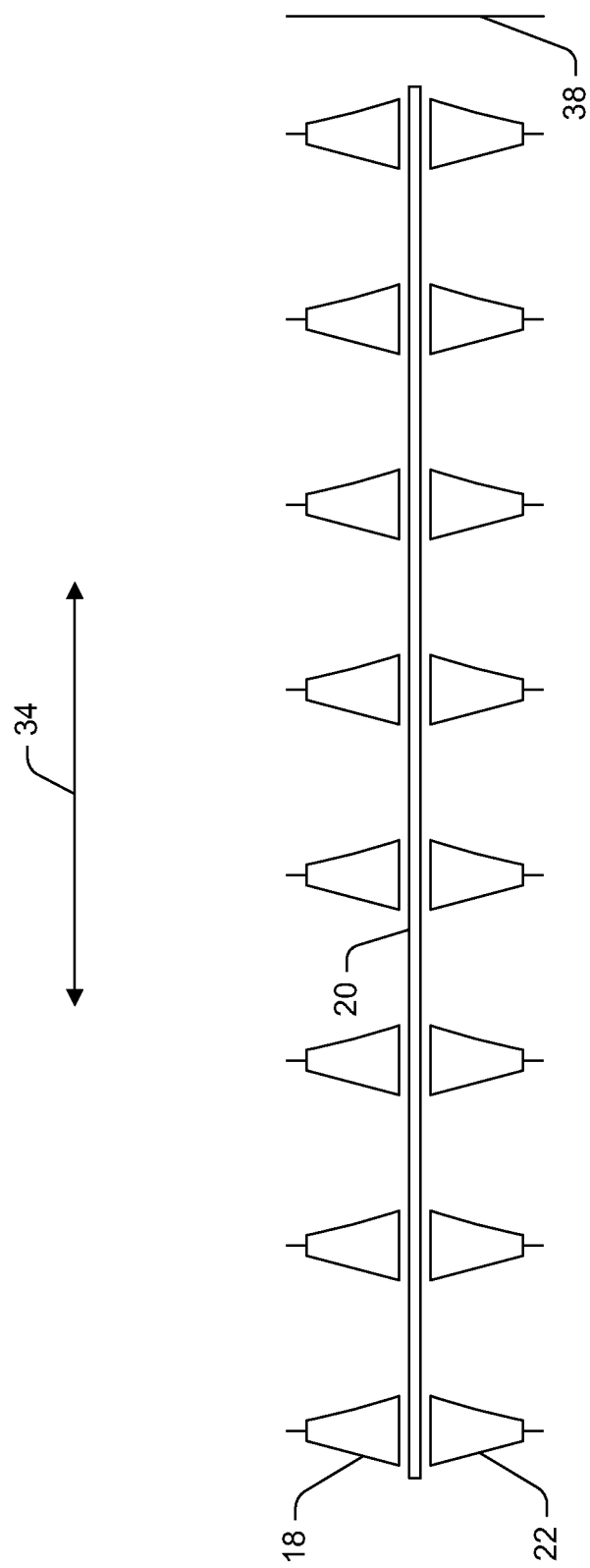
FIG. 2 illustrates an example horn pair arrangement in a system for inline fabric conductivity measurement.

FIG. 2 illustrates such an arrangement in cross section, with eight horn pairs 18, 22 arrayed across the width of material 20. The greater the density of horn pairs in the width dimension 34, the more complete the inspection coverage. The horn pairs can yield transmission measurements across substantially the entire width of the material. By this it is meant that the placement of horn pairs across the width of the material provides coverage for no less than eighty percent of the width of the material. In some examples, one-hundred percent coverage can be achieved by appropriate placement and density of microwave horns. In addition to the microwave transmit/receive horn pairs used to collect microwave transmission data, an additional channel 38 can be shorted to provide a zero response. The additional channel zero response can be used to measure drift of the system over time.

Unlike the example in FIG. 1, in the example in FIG. 2, no horn pairs are arrayed along the length dimension 36. However, referring again to FIG. 1, multiple horn pairs can be placed along the length dimension 36 to provide measurement redundancy and/or greater measurement density in the length dimension 36. Horn pairs spatially separated from each other in the length dimension 36 can, for example, generate redundant measurements, or can generate measurements in alternative microwave polarity orientations.

Although the placement of the horns 18, 22 is illustrated with transmit horns 18 above the material 20 and receive horns 22 below the material 20, the horns can be arranged in other ways as well. For example, the transmit horns 18 can be below the material 20 and the receive horns 22 can be above the material 20. As another example, adjacent pairs of transmit/receive horns 18, 22 can alternate side placement, such that one transmit horn 18 is next to one receive horn 22 above the material 20 while the one transmit horn's receive horn mate is next the one receive horn's transmit horn mate below the material 20. Such alternating placement may, again, serve to reduce the possibility of stray microwave radiation causing channel crosstalk.

The horn pairs 18, 22 can also be polarized, having an orientation for an E-field and an H-field. As material 20 moves through the production line, an individual horn pair can detect conductivity in either a first E-field oriented in one direction or a second E-field oriented 90 degrees to the first E-field. The horns 28, 22 can be arranged such that measurements for both orientations are collected for the same general area of material 20. Because system 10 can collect microwave transmission data at multiple orientations, system 10 is able to measure the conductivity of the material in multiple directions and determine for any given point on the material 20 whether the material 20 is more conductive in one direction versus another.

Rather than activating the transmitters on all the channels simultaneously, the action of RF switch 16 can provide a "channel hop" that activates only one transmit-receive horn pair at a time, the horn pairs being rapidly activated and deactivated in a sequential order, thus avoiding crosstalk between channels. In additional to the channel hop, the action of microwave signal source 14 can further provide a rapid "frequency hop" whereby any individual channel corresponding to any particular transmit-receive pair might be tested at multiple frequencies by adjusting the frequency of microwave energy provided to any particular transmit horn 18. For example, measurements can be made for at least two frequencies per horn pair. As another example, measurements can be made for at least three frequencies per horn pair. As another example, measurements can be made for at least four frequencies per horn pair.

As an alternative to a frequency hop, wherein a set of discrete frequencies are tested over a range, a frequency sweep may be made, wherein a continuous range of frequencies is tested by continuous adjustment of the transmission frequency during activation. The particular frequencies or frequency ranges measured can be selected to cover frequency ranges of interest for any particular material 20 being measured.

The activation of any particular transmit/receive horn pair at a particular frequency or a particular frequency sweep range is referred to herein as a "burst." Sufficient buffer time can be permitted to elapse between the end of one burst and the start of the next, i.e., between the deactivation of the transmitter in one channel and the activation of the transmitter and/or receiver in the next channel in the sequence, to permit emitted energy to dissipate and thus avoiding corruption of one channel's measurement by previous-channel measurement energy. In some examples, the time needed to complete a burst can be less than one millisecond. In some examples, the time needed to complete a burst can be less than one microsecond.

The activation of a plurality of transmit/receive horn pairs in sequence at a variety of frequencies or frequency sweep ranges is referred to herein as a "burst set." A burst set may consist of, for example, a single activation of each pair (i.e., each channel) at each of a configurable predetermined number of frequencies. For example, a burst set may involve activating eight horn pairs at each of four frequencies for a total of thirty-two independent measurements. Such burst sets may be repeated to provide complete inspection coverage with measurements made at intervals of reliable uniformity.

System 10 can therefore collect microwave transmission data at multiple frequencies, at multiple points along the width of the material 20, at multiple orientations, at production-line speeds. For example, measurements of at least four different frequencies and of at least two different orientations can be conducted at material 20 speeds of twelve feet per minute or more.

The processor-based controller 12 can monitor the material feed via an encoder 28, can initiate hopping, via RF switch 16, of the transmit-receive pairs after a either a configurable predetermined time or a configurable predetermined travel interval, and can collect and store the transmission signal levels, as detected by power sensor 26. Measurements, either as individual bursts or as burst sets, can be repeated periodically or randomly during spooling of the material 20. The processor-based controller 12 can convert the measured signals, as detected by power sensor 26, into surface resistance values. Processor-based controller 12 can be, for example, a PC or other general-purpose computer system, or a special-purpose electronic digital controller.

In some instances the processor-based controller can initiate a new burst or a new burst set according to periodic timing, while in other instances the processor-based controller can initiate a new burst or a new burst set according to a travel interval of the material under measurement. As examples of travel interval measurement control, the controller can initiate a new burst set for every six inches of material travel along the production line, or for every three inches of material travel.

Microwave signal source 14 can be a signal generator capable of generating signals of specified frequencies between about 100 MHz to 30 GHz. Microwave signal source 14 thus can provide frequency hopping as well as signal generation. In some examples, microwave signal source 14 can be a free-running oscillator running at a fixed frequency, in which case, no frequency hopping will be provided.

Controller 12 can include a multifunction interface (not shown) as an intermediate between controller 12 and other components, e.g., sensor 26. Controller can also include or be linked to a user interface 32 which includes input and output devices for production line operator control and communication with system 10. The user interface 32 can include any of one or more of visual displays and/or rendering devices, audio outputs such as speakers or headphones, audio inputs such as microphones, visual inputs such as video cameras, and/or manual inputs such as keyboards and/or pointing devices such as computer mouses, trackballs, touchpads, or touchscreens.

For example, sampling data from any or all of the channels can be provided to a screen display for real-time viewing by an operator. The sampling data can additionally or alternatively be recorded to a memory as a data file in a data file format, for example, ".csv" file format. Such a memory can be included in controller 12 or can be external to controller 12. The user interface can be used to perform management of generated data files. Such management can include an initial setup indicating the particular data to be stored, the arrangement of the data, the analysis, if any, to be performed on the data. Other management performable through user interface 32 can include indicating the format of any marks or labels to be generated by marker/labeler 38.

Encoder 28 can provide processor-based controller 12 with an input indicative of production line speed, permitting controller 12 to control microwave signal source 14 and RF switches 16 and 24 so as to generate an appropriate number of measurement signals per unit distance of material travelled in length dimension 36. For example, controller 12 can speed or slow the rate at which measurements are made so as to provide two sets of measurements per foot of material 20, wherein a "set" consists of measurements from every transmit/receive horn pair (and thus at each desired orientation) at every desired frequency or frequency range. When the production line is running slower, e.g., less than twelve feet per minute, controller 12 can order more measurements and average successive measurements together for more accurate output. When the production line is running faster, e.g., more than twelve feet per minute, controller 12 can reduce the number of measurement cycles ordered per lengthwise foot of material 20.

The inline fabric conductivity measurement system 10 can be "inline" in that it can be placed in line with the production process used to fabricate the material 20, and can be non-destructive in that its measurement does not require cutting out samples of the material 20. As such, it is capable of testing the entirety of the produced material 20. An alternative to non-destructive inline measurement might involve excising a small portion of a fabric sample for measurement inside of an enclosure lined with absorber, such as a pyramid foam tailored to absorb energy in, for example, X and/or Ku bands.

While such a measurement method might yield a cleaner measurement signal for any individual sample, the measured microwave transmission data being freer of noise and interference and thus providing better bottom-end performance, such a method requires at least partial destruction of a fabricated roll in order to obtain the measurement sample. Furthermore, such a method is unable to test an entire roll without completely destroying the roll. Still further, such a method does not lend itself to rapid adaptability of manufacturing parameters and settings since it is performed after, as opposed to during, production of the roll. Yet still further, such a method is incapable of marking individual portions of a roll as it is being produced, where such marking might be indicative of roll quality.

For example, small portions of a long roll not meeting specified production tolerances could not be readily flagged using an enclosure-measurement method. The systems and methods of the present invention, by contrast, permit for non-destructive testing and can permit for rolls of arbitrarily large size to have sections of arbitrarily small sizes individually labeled with markers indicative of production runtime test results. Furthermore, the systems and methods of the present invention can be employed in an open manufacturing area without requiring costly absorber material.

The more highly conductive the fabricated material 20 is, the less microwave energy is transmitted through the material, and the more microwave energy is reflected off the surface of the material, during any particular test transmission. When the material 20 is a conductive fabric, very little energy can be expected to transmit through to the receive horn 22.

The inline fabric conductivity measurement system 10 can provide a quality assurance (QA) system for production of conductive fabrics such as fiber-mats and composite prepregs. The system 10 can be a standalone sensor assembly that can be adapted to commercial fabric production machine. The manufactured material 20 can be inspected as it passes through the system's sensor assembly in front of the collection spool 30. The system 10 can sample the width and length of the entire spool 30 of material at regular intervals and can record the results on, for example, a non-transitory computer-readable memory, such as a magnetic media. Based on the test data, pass/fail conditions and problem areas may be established.

Controller 12 can analyze the results of measurements to determine the quality of individually measured portions of material 12 for satisfactory or defective conductivity properties. In a simple example of such analysis, controller 12 can compare measured transmission values to predefined thresholds. In another example, controller 12 can perform statistical analyses on collected data to test for disuniformities in conductivity known to be associated with manufacturing defects. In another example, controller 12 can compare measured transmission values from one orientation to measured transmission values from another orientation to obtain a measure of anisotropy, which measure can be compared to a predefined threshold. In another example, controller 12 can perform statistical analyses on such derived anisotropy measures to test for disuniformities in conductivity known to be associated with manufacturing defects. In some examples, the controller can analyze for unacceptable variability in measurements over the length and/or width of material 20, e.g., by computing statistical measures and comparing those measures against thresholds.

The analysis can indicate defects in material 20. Such defects can include holes in the material 20, wrinkles in the material 20, or unexpectedly high or low conductivity in one orientation or another. Such defects can be marked or flagged on the material, can alert a production operator to make immediate changes in the production process, and/or can be used to determine the source of a defect or the reason for its correction at various phases in a multi-phase production process.

The analysis can be performed in real-time, i.e., substantially simultaneously with the measurement process, such that marker/labeler 38 can mark or label material 20 as it passes in the production line before being rolled into roll 30. Marker/labeler 38 can mark or label material 20 in accordance with the performed analysis in a variety of different ways. In some examples, marker/labeler 38 can consist of a printer or engraver that can print or engrave output marks directly onto the material 20. An engraver can be, for example, a laser engraver. The output marks can be indicative of measured values or of determinations of material quality derived from the analysis. As such, the output marks can range from detailed numerical descriptions to simpler marks that serve only to flag defective portions of material 20. Rather than marking on the material 20, marker/labeler 38 can label the material, as by "bookmarking" defective material 20 portions, for example, by using lightly adhesive slips of paper or other thin material, to flag defective portions of material 20. The labels can, for example, extend past a widthwise edge of the material 20, such that the labels and their positions on the material 20 are clearly visible even when material 20 is rolled up into roll 30.

Analysis results can also be displayed for a production line operator on a display included in user interface 32. The displayed information can take the form of raw measurement data, analyzed results, and/or alerts that can communicate to an operator when adjustments should be made to the production process to preserve consistency of production quality in material 20. In addition to any real-time analysis performed to flag defects and control production parameters during fabrication of a single roll 30 of material 20, storage and post-processing of collected measurement data can be used to compare production roll-to-roll, batch-to-batch, day-to-day, month-to-month, or over longer periods. In this manner, "creep," i.e., production changes that may be too subtle to generate an alert or cause a portion of a roll to be flagged as defective, can be tracked and noted over longer periods of time. Likewise, various materials and other production inputs can be quantitatively compared.

A simple numerical example for display of real-time data might consist of a number of boxes, or a table of a number of columns, the number of boxes or columns corresponding to the number of channels in the measurement system. With each burst set, the values in the boxes or display tables may be updated. The same data may also be displayed graphically, as a chart, graph, map, or other rendering. In the case of a graph of the data values on an axis, corresponding to either time or material travel distance depending on the manner in which measurements are triggered by controller 12, upper and/or lower limits may be shown on the graph for the benefit of production line operators, who may be advised when rendered conductivity measurement traces exceed or fall below established upper or lower limits, respectively.

The measurement system 10 may also be portable, such that it can be easily disengaged from the production line and moved to another production line or another location. In such examples, the horns may be provided in an integrated, modular unit. Such a unit can be shaped as a two-tined fork, with upper horns arranged on an upper tine and lower horns arranged on a lower tine, the material traveling between the tines. Such a portable measurement system may be easily disengaged and removed from a production line without requiring removal of production material from the production line.

Figure 3:
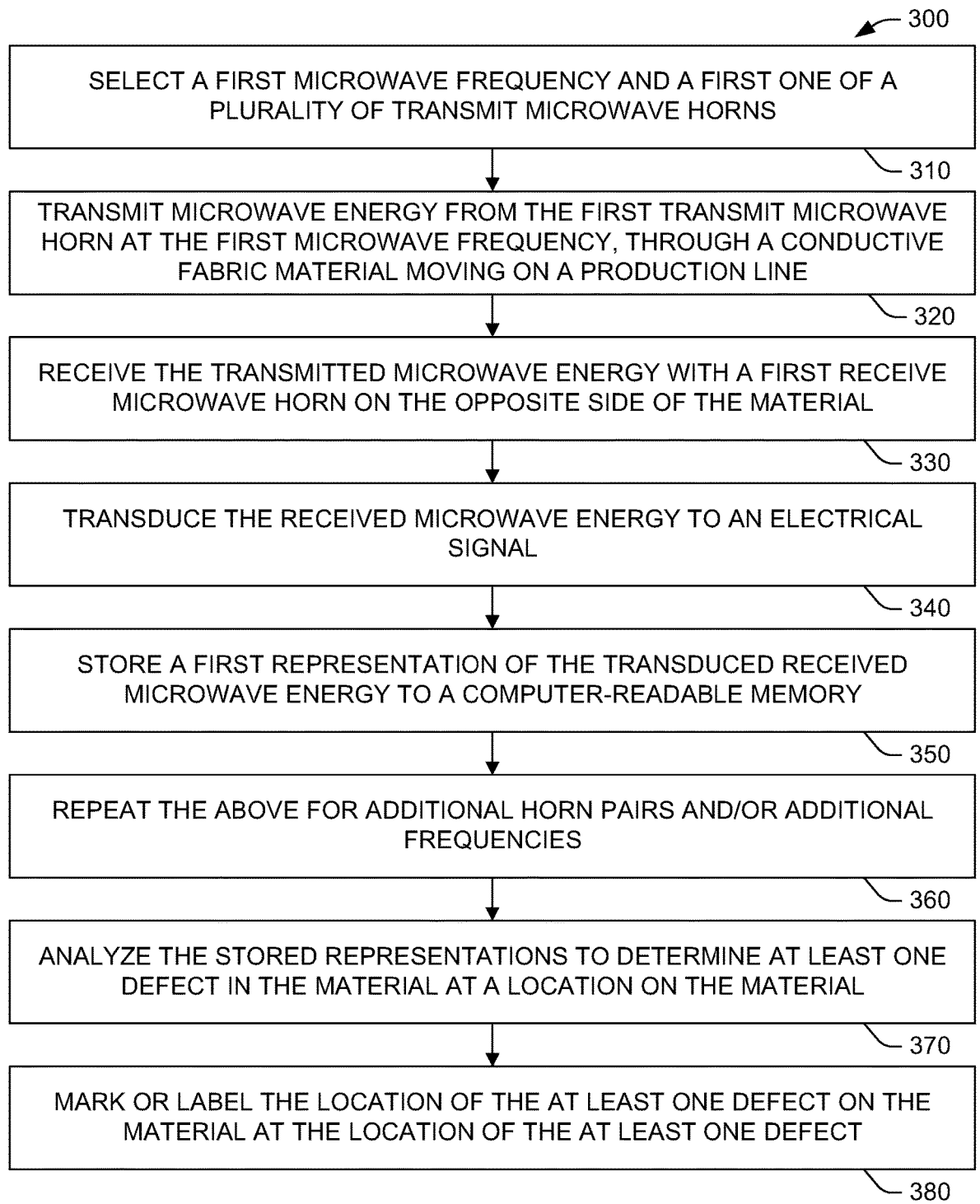
FIG. 3 is a flow chart showing an example method of inline fabric conductivity measurement.

FIG. 3 is a flow chart illustrating an example method 300 for non-destructive, inline, multi-channel fabric conductivity measurement. The method 300 can begin by selecting 310 a first microwave frequency and a first one of a plurality of transmit microwave horns. A processor-based controller, such as controller 12 illustrated in FIG. 1, can be used to perform the selection in an automated fashion. For example, the controller can select the frequency and transmit horn from among a those in a programmed sequence, and can move sequentially through the available horns and frequencies.

The method 300 can continue by transmitting 320 microwave energy from the first transmit microwave horn at the first microwave frequency, through a conductive fabric material moving on a production line. Next, the method can involve receiving 330 the transmitted microwave energy with a first receive microwave horn. The first receive microwave horn can be placed to be paired with the first transmit microwave horn, as being opposed to the first transmit microwave horn on the opposite side of the material from the first transmit microwave horn. The first transmit and receive microwave horns can be said to form a first horn pair.

The method 300 can continue with the transduction 340 the received microwave energy into, for example, an electrical signal, and storing 350 a first representation of the transduced received microwave energy to a computer-readable memory. The storing can be done, for example, by the controller, and the memory can be included in the controller.

The selecting 310, transmitting 320, receiving 330, transducing 340, and storing 350 can be repeated 360 for a second horn pair comprising a second transmit microwave horn and a second receive microwave horn to yield a second stored representation. In some examples, the method can be repeated for additional horn pairs, for example six horn pairs, eight horn pairs, or ten horn pairs. The method may also repeat 360 the selecting 310, transmitting 320, receiving 330, transducing 340, and storing 350 for various additional frequencies or frequency ranges. Thus, each transmit horn might transmit multiple times over the course of the method, each time at a different frequency and each time at the same general location of the material. Because the measurement cycle 310-350 can happen very fast, on the order of milliseconds or microseconds, the location of different frequency measurements by a single horn pair may differ by very little, within an acceptable tolerance, even when the material moves very quickly on the production line, for example, twelve feet per minute. Such acceptable tolerances may be, for example, differences of two inches or less. For example, an acceptable tolerance might be one inch difference or less in location between different frequency measurements.

As described previously, when the microwave energy transmitted between the first horn pair is polarized in a first orientation and the microwave energy transmitted between the second horn pair is polarized in a second orientation 90 degrees from the first orientation, a comparison between the first stored representation and the second stored representation can give a measure of the anisotropy of the material.

In some instances the method 300 can further include analysis 370 and marking or labeling 380. For example, the method 300 might further include analyzing 370 the stored representations to determine at least one defect in the material at a location on the material. Such analysis 370 might be performed, for example, by controller 12 illustrated in FIG. 1. As discussed previously, the analysis might consist of computing one or more statistical measures. Such measures may include finding high, low, and mean values of conductivity measurements, for each individual channel or for all channels.

Such analysis 370 might also consist of applying various filters to the data, for example to smooth the data, so as to provide an output more reliably indicative of unacceptable deviation. It may be, for example, that an occasional spike in measured conductivity may be tolerable, so long as it is not larger than a predetermined amplitude or does not last for too long in the production run. Smoothing the measured data may filter out such tolerable spikes and thus prevent an unnecessary alarm condition or flagging of defective material.

Such analysis 370 might also consist of computing other metrics, such as counting spikes in conductivity measurements. It may be that an occasional spike may be tolerable but a predetermined number of spikes within a predetermined length of material should signal an alarm condition or be flagged as a defect. While analysis of filtered (e.g., smoothed) measurement data may permit for repeated spikes to go unobserved, other numerical analyses of the data, such as spike counting, may provide necessary insights into production quality.

Such analysis 370 might also consist of generating one or more histograms to graphically display conductivity variability. Such histograms can be displayed and updated in real time as measurements are collected, or can be generated from accumulated, stored measurement data following a production run.

The method 300 might also further include marking or labeling 380 the location of the at least one defect on the material at the location of the at least one defect, as the material moves on the production line. The marking or labeling might be performed by a marker or labeler, such as marker or labeler 38 shown in FIG. 1. The marking or labeling can be based on a signal from the controller, which can, in turn, be based on the analysis performed earlier 370. In other words, the controller can recognize the defect and direct the defect to be so labeled.

Example methods similar to method 300 might include storing in the memory a zero response from a shorted channel and characterizing drift over time in the stored representations of microwave transmissions between the horn pairs based on the stored zero response from the shorted channel.

Material quality for individual rolls can also be carefully compared using multiple systems 10 of the present invention placed at separate production lines or separate parts of an individual production line. For example, one system 10 can collect data while a roll of material is initially fabricated produced while the same or another system 10 can collect data during a later production stage, e.g., while the produced material is prepregged with resin. During any individual phase of production a material may be compressed or stretched which may affect its conductivity or anisotropy. The prior and later collected measurement data can be compared to detect whether a defect arose during the earlier production process, during the later production process, or some time in between, as during storage or shipment. The comparison can also indicate that an earlier-detected defect was corrected in a later stage of the production process. Such a comparison can be useful, for example, in assigning fault between multiple material suppliers and in correcting difficult-to-track production problems in large production systems involving numerous production plants.

Figure 4:
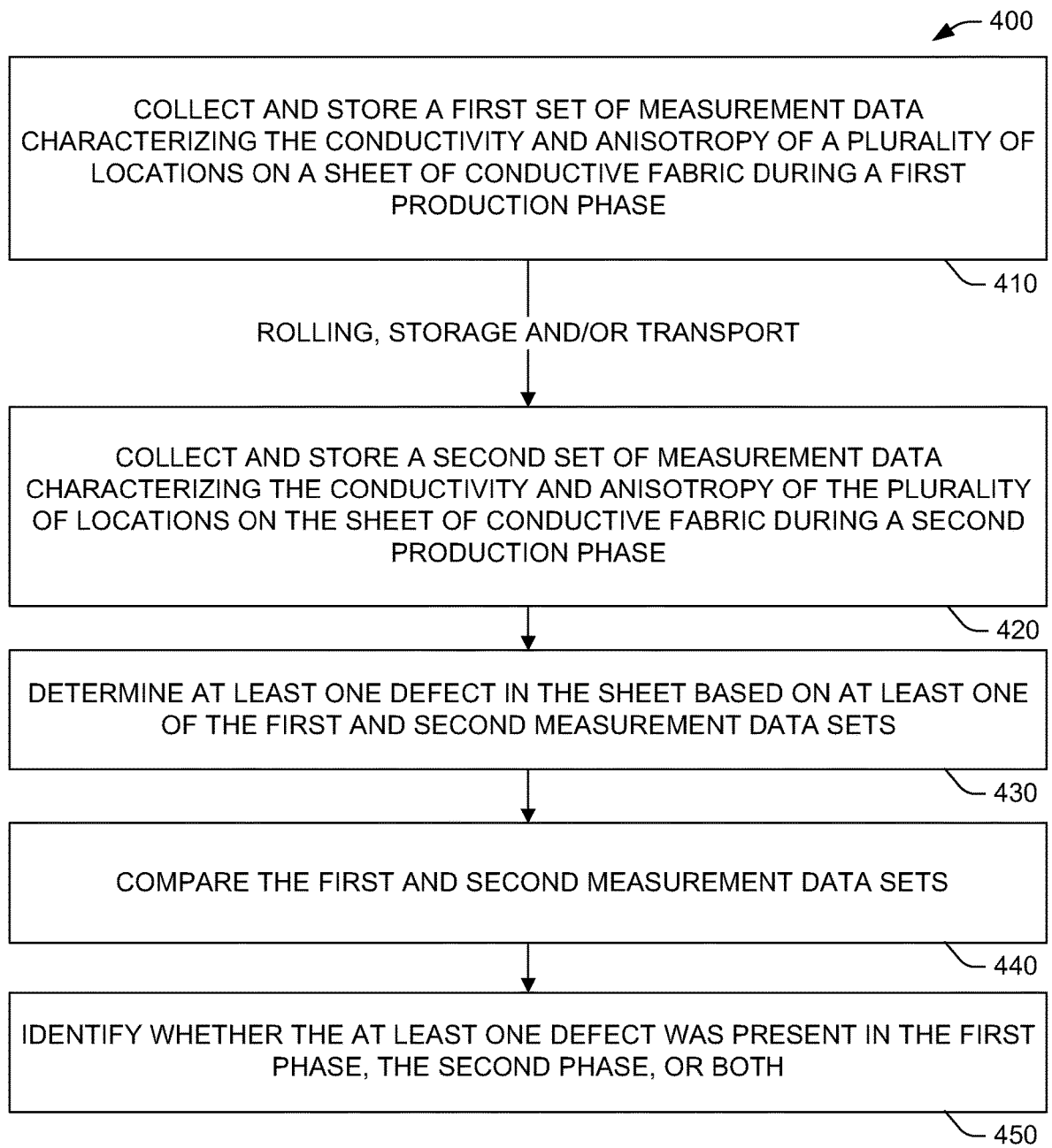
FIG. 4 is a flow chart showing an example method of identifying a source of a defect in a manufacture of conductive fabric.

FIG. 4 is a flow chart illustrating an example of such a method 400 of identifying a production phase as a source of a defect in a manufacture of conductive fabric. First, during a first phase of manufacture of the sheet, the method can include collecting and storing 410 a first set of measurement data characterizing the conductivity and anisotropy of a plurality of locations on a sheet of conductive fabric. The sheet of conductive fabric can be greater than one hundred feet in length and can potentially be many hundreds or even thousands of feet in length. The measurement data can be based on detected microwave transmittance between a plurality of microwave transmit/receive horn pairs, each horn pair comprising a transmit horn and a receive horn positioned to oppose each other on opposite sides of the sheet, as in the systems illustrated in FIGS. 1 and 2 and described previously.

In between the first production phase and a second production phase, the sheet of conductive fabric might be rolled up into a roll, stored, and/or transported, perhaps over long distances. Each of the rolling, storage, and/or transport might introduce defects, or the defects may have been introduced during phases of the manufacturing process, and it may be difficult to determine at what stage the defects may have been introduced.

During a second production phrase, which may be, for example, a prepreg phase, the method can continue with collecting and storing 420 a second set of measurement data characterizing the conductivity and anisotropy of the plurality of locations on the sheet. At least one defect in the sheet may be determined 430 based on at least one of the first and second measurement data sets, which can be compared with each other 440 to identify 450 whether the at least one defect was present in the first phase, the second phase, or both.

Production issues can be corrected in a variety of ways. The following provide just a few examples. The compositions and/or concentrations of chemical feedstocks to the production process can be changed or adjusted. Adjustable parameters on the production line equipment can be optimized. Environmental parameters such as temperatures, pressures, and humidities can be adjusted. Malfunctions in the production equipment can be detected for repair. The precise nature of corrections that can be made to ameliorate or eliminate defects in produced material will depend on the nature and type of equipment and diagnosis of the causes of the specific flaws detected by using the test systems and methods described herein. The present systems and methods can provide useful insight to production operators and specialists to determine the nature and sources of defects, and/or to eliminate from suspicion certain equipment and production phases as the potential causes of such defects.

The present systems and methods fulfill a need to non-destructively measure for electrical properties a moving continuous material in a manufacturing line so as to provide complete inspection of the material, which can be many hundreds of feet long. Because the present systems and methods can make measurements in multiple polarities, they are capable of inspecting for deviations and defects in expected material anisotropy. The systems and methods are also capable of inspecting material that can be very wide, for example, fifty-four inches in width, by using multiple channels to map the width to ensure all of the material is within specification, and not just a specific location. The testing systems and methods can produce, for example, six, eight, or ten channels of data taken at multiple spots per foot of material in a continuous fashion. The described systems and methods can also make measurements not only at a single frequency of interest but over a range of frequencies that cover the use of the material.

The described systems and methods can perform 100% surface inspection before shipping of the finished product to the end users. The systems and methods therefore can provide more complete quality assurance, problem area identification, and early detection and correction of production issues during the manufacture of material at two or more different phases in the manufacturing process, such as before and after a prepreg.

The described methods and systems do not require direct sensor contact with the material under test. As such, the described methods and systems are much less likely to cause contamination of or damage to the material under test. Additionally, the described methods and systems are capable of detecting orientation of conductive fibers in a tested material, unlike with eddy current or optical transmission methods that may be used to measure coating conductivity of homogeneous thin films such as vapor deposition coatings. Finally, because the described methods and systems use arrays of microwave horn pairs, they do not require servo mechanisms and the associated complicated controls to mechanically move sensors across a material in a scanning fashion.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

We claim:

1. A non-destructive, inline, multi-channel fabric conductivity measurement system comprising:
 a processor-based controller communicatively coupled to
  a microwave signal source configured to produce signals at frequencies specified by the controller, and a transmit radio frequency (RF) switch configured to select one of a plurality of transmit microwave horns arranged in an array and route signals from the microwave signal source to a selected one of the plurality of transmit microwave horns;

an encoder configured to measure a speed of a production line configured to feed a fabric material between a plurality of pairs of opposing microwave horns, the production line comprising, on one side of the material, the transmit microwave horns and, on an opposing side of the material, a plurality of receive microwave horns arranged to each oppose a corresponding one of the transmit microwave horns, the encoder further being configured to transmit the measured speed to the controller, wherein the controller is configured to receive and record transmission measurements from at least one power sensor, the measurements corresponding to signals received from one of the plurality of receive microwave horns during periods of transmission from the transmit microwave horns, and wherein the controller controls the microwave signal source and the transmit RF switch based on the production line speed.

2. The system of claim 1, wherein the controller is further communicatively coupled to a receive RF switch configured to select one of the plurality of receive microwave horns, the receive RF switch being coupled to the at least one power sensor, and wherein the controller is further configured to control the receive RF switch based on the production line speed.

3. The system of claim 1, wherein the controller is further communicatively coupled to a marker or labeler configured to mark or label the material with marks or labels indicative of material quality or defects in the material as the material moves on the production line.

4. The system of claim 3, wherein the marker or labeler is a labeler configured to label the material with adhesive labels that extend past the widthwise edge of the material.

5. The system of claim 3, wherein the marker or labeler is a printer configured to print indicators of material quality or defects onto the material.

6. The system of claim 3, wherein the marker or labeler is a laser engraver configured to engrave indicators of material quality or defects onto the material.

7. The system of claim 1, wherein at least two opposing pairs of transmit/receive microwave horns are arranged per foot of width of the material.

8. The system of claim 1, wherein at least eight opposing pairs of transmit/receive microwave horns are arranged per foot of width of the material.

9. The system of claim 1, wherein for at least one of the opposing pairs of microwave horns, the transmit horn is placed within ten millimeters of one side of the material, without touching the material, and the receive horn is placed within ten millimeters of the opposite side of the material, without touching the material.

10. A method for non-destructive, inline, multi-channel fabric conductivity measurement, the method comprising:

a processor-based controller selecting a first microwave frequency and a first one of a plurality of transmit microwave horns;

transmitting first microwave energy from the first transmit microwave horn at the first microwave frequency, through a conductive fabric material moving on a production line;

receiving the transmitted first microwave energy with a first receive microwave horn placed to be paired with the first transmit microwave horn as being opposed to the first transmit microwave horn on an opposite side of the material from the first transmit microwave horn, the first transmit and receive microwave horns forming a first horn pair;

transducing the received first microwave energy and storing, by the processor-based controller, a first representation of the transduced received microwave energy to a computer-readable memory;

the processor-based controller selecting a second microwave frequency, either the same as or different from the first microwave frequency, and a second one of a plurality of transmit microwave horns, different from the first one of the plurality of transmit microwave horns;

transmitting second microwave energy from the second transmit microwave horn at the second microwave frequency, through the conductive fabric material moving on the production line;

receiving the transmitted second microwave energy with a second receive microwave horn placed to be paired with the second transmit microwave horn as being opposed to the second transmit microwave horn on the opposite side of the material from the second transmit microwave horn, the second transmit and receive microwave horns forming a second horn pair;

transducing the received second microwave energy and storing, by the processor-based controller, a second representation of the transduced received second microwave energy to the computer-readable memory.

11. The method of claim 10, wherein the first microwave energy transmitted between the first horn pair is polarized in a first orientation and wherein the second microwave energy transmitted between the second horn pair is polarized in a second orientation 90 degrees from the first orientation, and the placement of the first and second horn pairs and the time difference between the transmitting the first microwave energy and the transmitting the second microwave energy is such that a comparison between the first stored representation and the second stored representation gives a measure of the anisotropy of the material.

12. The method of claim 10, wherein the selecting, transmitting, receiving, transducing, and storing are repeated for at least four additional horn pairs, the horn pairs being spaced across the width of the material so as to yield transmission measurements across substantially the entire width of the material.

13. The method of claim 12, wherein the selecting, transmitting, receiving, transducing, and storing are repeated for at least two additional selected frequencies different from the first selected frequency and from each other.

14. The method of claim 13, wherein the microwave energy transmitted between a first plurality of horn pairs is polarized in a first orientation and wherein the microwave energy transmitted between a second plurality of horn pairs is polarized in a second orientation 90 degrees from the first orientation, such that a comparison between stored representations from the first plurality of horn pairs and stored representations from the second plurality of horn pairs gives measures of the anisotropy of the material at a plurality of locations across the material.

15. The method of claim 10, wherein the selecting, transmitting, receiving, and transducing are altogether completed in less than one millisecond for each horn pair.

16. The method of claim 10, further comprising:
the controller analyzing the stored representations to determine at least one defect in the material at a location on the material; and
a marker or labeler marking or labeling the location of the at least one defect on the material at the location of the at least one defect, as the material moves on the production line, based on a signal from the controller.

17. The method of claim 10, further comprising:
storing in the memory a zero response from a shorted channel; and
characterizing drift over time in the stored representations of microwave transmissions between the horn pairs based on the stored zero response from the shorted channel.

18. A method of identifying a source of a defect in a manufacture of conductive fabric, the method comprising:
collecting and storing a first set of measurement data characterizing respective conductivities and respective anisotropies of a plurality of locations on a sheet of conductive fabric greater than one hundred feet in length during a first phase of manufacture of the sheet, the measurement data based on detected microwave transmittance between a plurality of microwave transmit/receive horn pairs, each horn pair comprising a transmit horn and a receive horn positioned to oppose each other on opposite sides of the sheet;
collecting and storing a second set of measurement data characterizing respective conductivities and respective anisotropies of the plurality of locations on the sheet during a second phase of manufacture of the sheet;
determining at least one defect in the sheet based on at least one of the first or second measurement data sets;
identifying whether the at least one defect was present in the first phase, the second phase, or both, based on a comparison of the first and second measurement data sets.

19. The method of claim 18, wherein the second phase is a prepreg phase.

20. The method of claim 18, wherein the sheet is stored in a roll between the first and second phases.

* * * * *